United States Patent [19]

Miano et al.

[11] 4,276,387
[45] Jun. 30, 1981

[54] UREAS CONTAINING THE 2,2,2-TRICHLOROETHYL GROUP AS FLAME RETARDANTS FOR POLYURETHANE FOAMS

[75] Inventors: Jeffrey D. Miano, Havertown; Stanley R. Sandler, Springfield, both of Pa.

[73] Assignee: Pennwalt Corporation, Philadelphia, Pa.

[21] Appl. No.: 144,751

[22] Filed: Apr. 28, 1980

[51] Int. Cl.³ ............... C08G 18/14; C08G 18/32; C08G 18/50; C07C 127/15
[52] U.S. Cl. ................... 521/167; 564/60; 564/61; 521/115
[58] Field of Search ............ 521/167; 260/553 R; 564/60

[56] References Cited

U.S. PATENT DOCUMENTS 3,981,913  9/1976  Markiewitz .................. 528/262

*Primary Examiner*—H. S. Cockeram

[57] ABSTRACT

A compound of Formula I:

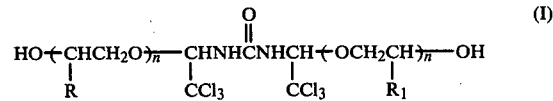

is useful as flame retardants for polyurethane foams. It is added directly to the reaction mixture for the preparation of the polyurethane foam.

9 Claims, No Drawings

UREAS CONTAINING THE 2,2,2-TRICHLOROETHYL GROUP AS FLAME RETARDANTS FOR POLYURETHANE FOAMS

BACKGROUND OF THE INVENTION

1. Field of the Invention

This invention relates to a urea compound containing the 2,2,2-trichloroethyl group that is useful as a flame retardant for polyurethane foams.

2. Description of the Prior Art

U.S. Pat. No. 4,152,497 teaches flame retarded polyurethane foams using compounds containg 2,2,2-trichloroethyl groups. These compounds are permanently bound into the polymer in the same manner as the instant application. The problem with the compounds of this patent is that the compounds are solids and have limited solubility in the polyol used to prepare the polyurethane. Thus the composition of the prior art are difficult to use as an ingredient in the formulation for preparing the polyurethane.

The compound of the present invention overcomes this disadvantage of the prior art because they are either liquids or more soluble solids and can be easily used to formulate with polyols used in preparing the polyurethane.

STATEMENT OF THE INVENTION

The present invention is directed to a compound having the Formula (I)

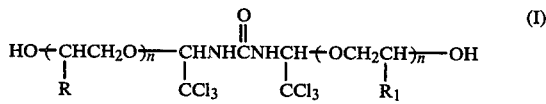

wherein R and $R_1$ are independently selected from the group consisting of hydrogen, $-CCl_3$, $-CH_3$ and $-CH_2CCl_3$ and n is an integer of 1 to 100 (preferably 1 to 20).

This invention also is directed to a flame retarded polyurethane foam prepared from a reaction mixture which comprises a flame retarding amount of a compound of Formula (I).

DETAILED DESCRIPTION OF INVENTION

The compound used as the flame retardant additive of this invention may be prepared by the reaction of urea with chloral or chloral hydrate. The urea compound is stirred with chloral or chloral hydrate in a solvent at 25° to 150° C., preferably 70° to 90° C., to produce the desired reaction product. The reaction product is then further reacted with various unsubstituted or halogen substituted epoxides to increase the molecular weight of the flame retardant and/or increase the halogen content. Epoxides useful for these purposes include ethylene oxide, propylene oxide, 3,3,3-trichloro-1,2-propylene oxide, and 4,4,4-trichloro-1,2-butylene oxide.

Representative structures of the compound of the instant invention of Formula (I) are:

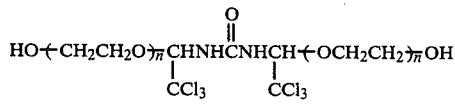

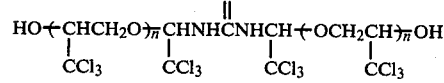

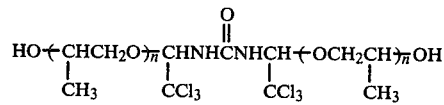

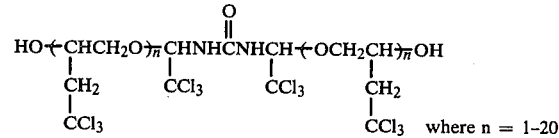

where n = 1–20

The most common types of polyurethanes are formed by the reaction of toluene diisocyanate (TDI) or polymethylene polyphenylisocyanate or mixtures thereof, with polyfunctional hydroxy compounds. The flame retardant additives described in this invention (see Formula I) are effective as flame retardants for hot cure flexible polyurethane foam, high resiliency polyurethane foam, rigid polyurethane foam, and rigid polyurethane/isocyanurate foam copolymers. These additives are especially effective as flame retardants for polyurethane foam.

This compound is added to the reactants for preparing the polyurethane foams in the amount of 1 to 80 parts per hundred parts of the polyol (php) component by weight to impart flame retardancy. The preferred loading and high resiliency polyurethane foam is 0.5 to 5.0 php by weight and for rigid polyurethane foam is 5–70 php.

The following examples illustrate the present invention but are not intended to limit the invention thereto.

Polyurethane foams described in the following examples are made by mixing the liquid flame retardant additive in the polyol followed by addition of catalysts, surfactant, water and/or blowing agent and isocyanate as described by J. H. Saunders and K. C. Frisch in "Polyurethanes: Chemistry and Technology", Interscience, New York, 1964. In the case of flexible foams, this mixture is stirred by a high speed mixer and is poured into a thirteen inch by thirteen inch by five inch mold which may or may not be clamped shut. After the reaction is completed, the foam is removed and aged at room temperature for at least seven days (conventional "hot cure" foams are cured at 100° C. for ½ hour prior to aging). Rigid foams are made by pouring the stirred reaction mixture into an eight inch by eight inch by five inch box and allowing the reaction to proceed under "free rise" conditions. The flame retardant properties of the rigid foams are evaluated using ASTM D-1692-74.

EXAMPLE 1

Propylene Oxide Reacted with 1,3-Bis(2,2,3-Trichloro-1-hydroxyethyl)urea

Propylene oxide 500 g (8.6 moles) was added dropwise to a solution of 710 g (2.0 moles) of 1,3-bis(2,2,2-trichloro-1-hydroxyethyl)urea in 320 g of 50% NaOH solution. The temperature of the reaction mixture was brought up by the exotherm to 38° C. from room temperature, and the stirring was continued for a total of 4 hours. The reaction-mixture was then poured over 2500 g of ice and 500 ml of conc. HCl. The reaction product is a viscous liquid or a soft pasty solid was isolated, washed with H₂O, and dried at 60° C. for 10 hours.

The elemental analysis, and infrared spectrum were consistent with the assigned structure of the product.

EXAMPLE 2

A rigid polyurethane foam was prepared using the composition of Example 1 as follows:

|  | Parts by Wt. |
|---|---|
| Composition of Example 1 | 28.8 |
| Multranol E9221 Polyol (Mobay)[a] | 71.2 |
| DC 193 Surfactant (Dow Corning)[b] | 1.8 |
| Polycat 8 (Abbott)[c] | 1.0 |
| T-12 Catalyst (M&T)[d] | 0.1 |
| Isotron 11B Blowing Agent (Pennwalt)[e] | 36.0 |
| Mondur MR Isocyanate (Mobay)[f] |  |
| The reactivity parameters for the foam preparation are: |  |
| Cream Time (sec): | 24 |
| Gel Time (sec): | 50 |
| Tack-Free Time (sec): | 65 |
| Rise-Time (sec): | 70 |
| Physical Property: |  |
| Core Density (lb/ft³): | 2.2 |
| Flammability Property: |  |
| ASTM D-1692 (Inches Burned): | 3.0 |

[a] A sucrose/amine based polyol hydroxyl number = 475 mg KOH/g.
[b] A nonhydrolyzable silicone glycol copolymer.
[c] Dimethyl cyclohexylamine.
[d] Dibutyltin dilaurate.
[e] Trichlorofluoromethane with 0.25% alloocimine as an inhibitor.
[f] Polymethylene polyphenyl isocyanate.

EXAMPLE 3

A rigid polyurethane foam was prepared using no flame retardant; the flammability test results below show that the foam burns completely (5 inches) in the ASTM D-1692 test.

|  | Parts by Wt. |
|---|---|
| Multranol E-9221 (Mobay) | 100.0 |
| DC 193 | 1.8 |
| Polycat 8 | 1.0 |

|  | Parts by Wt. |
|---|---|
| T-12 | 0.1 |
| Isotron 11B | 36.0 |
| Mondur MR | 127.5 |
| The reactivity parameters for the foam preparation are: |  |
| Cream Time (sec) | 40 |
| Gel Time (sec) | 65 |
| Tack-Free Time (sec) | 75 |
| Rise-Time (sec) | 101 |
| Physical Property: |  |
| Core Density (lb/ft³) | 2.8 |
| Flammability Property: |  |
| ASTM D-1692 (Inches Burned) | 5.0 (Total sample burned) |

What is claimed:

1. A compound having the formula:

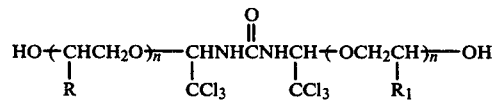

wherein R and R₁ are independently selected from the group consisting of hydrogen, —CCl₃, —CH₃ and —CH₂CCl₃ and n is an integer of 1 to 100.

2. The compound of claim 1 wherein R and R₁ are hydrogen, and n is 1–20.

3. The compound of claim 1 wherein R and R₁ are —CCl₃ and n is 1–20.

4. The compound of claim 1 wherein R and R₁ are CH₃ and n is 1–20.

5. The compound of claim 1 wherein R and R₁ are —CH₂CCl₃ and n is 1–20.

6. Polyurethane foam prepared from a reaction mixture which comprises a flame retardant amount of the compound of claim 1.

7. The polyurethane foam of claim 6 wherein the polyurethane foam is high resiliency foam.

8. The polyurethane foam of claim 6 wherein the polyurethane foam is hot cure flexible foam.

9. The polyurethane foam of claim 6 wherein the polyurethane foam is rigid foam.